(12) United States Patent
Weiss et al.

(10) Patent No.: US 6,492,561 B2
(45) Date of Patent: Dec. 10, 2002

(54) ALKALINE EARTH METAL ALKYLENE DIAMIDES, METHOD FOR THEIR PRODUCTION, AND THEIR USE

(75) Inventors: Wilfried Weiss, Oberursel (DE); Dirk Dawidowski, Frankfurt (DE)

(73) Assignee: Chemetall GmbH, Frankfurt am Main (DE)

( * ) Notice: Subject to any disclaimer, the term of this patent is extended or adjusted under 35 U.S.C. 154(b) by 0 days.

(21) Appl. No.: 10/057,781

(22) Filed: Jan. 25, 2002

(65) Prior Publication Data

US 2002/0151752 A1 Oct. 17, 2002

(30) Foreign Application Priority Data

Feb. 1, 2001 (DE) .......................................... 101 04 807

(51) Int. Cl.[7] ............................................. C07C 211/65

(52) U.S. Cl. ................. 564/511; 260/665 R; 423/245.1; 423/364; 423/351; 423/497; 568/671

(58) Field of Search ...................... 564/511; 260/665 R; 423/245.1, 364, 351, 497; 568/671

(56) References Cited

U.S. PATENT DOCUMENTS 4,555,498 A * 11/1985 Kamienski .................. 502/153

FOREIGN PATENT DOCUMENTS

WO 0023635 * 4/2000

* cited by examiner

Primary Examiner—Shailendra Kumar
(74) Attorney, Agent, or Firm—Fulbright & Jaworski L.L.P.

(57) ABSTRACT

Alkaline earth metal alkylene diamides of Ba, Sr, Ca and a method for their production.

13 Claims, No Drawings

ALKALINE EARTH METAL ALKYLENE DIAMIDES, METHOD FOR THEIR PRODUCTION, AND THEIR USE

BACKGROUND AND SUMMARY OF THE INVENTION

The invention relates to alkaline earth metal alkylene diamides, a method for their production, and their use.

The alkaline earth amides are strong metallizing agents and serve as, among other things, as starting materials for the production of alkaline earth metal oxides (M. F. Lappert et al., "Metal and Metalloid Amides," John Wiley & Sons, NY 1980).

The alkoxides (or alcoholates) of the alkaline earth metals find use, for example, as precursors for the production of thin metal oxide coatings (by the CVD or the sol-gel process) for electronic materials, especially high-temperature superconductors (W. A. Hermann, *Angew. Chem.* 1995, 107, 2371).

Alkaline earth alkoxides are also used as additives in the anionic polymerization of dienes with butyl lithium; here the addition of alkaline earth alkoxides brings about a high trans-content in the polymer, which has an advantageous effect on the properties of the end products, e.g. tires (U.S. Pat. Nos. 5,100,965, 4,020,115 and 3,992,561).

In addition, on account of their basic properties and often good solubilities in ethers and hydrocarbons, the alkaline earth alkoxides are also usable in many ways as reagents in deprotonization and alkoxylation reactions as well as condensations (D. C. Bradley, R. C. Mehrotra, D. P. Gaur, *Metal Alkoxides, Academic Press*, N.Y., 1978; U.S. Pat. No. 4,555, 498).

Methods for the synthesis of barium alkoxides, for example, which have been known heretofore start out from the metals:

the metal amides (the amide route):

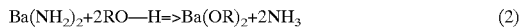

the metal iodides (salt metathesis):

Reaction (1) is very slow and leads to "complexes" $Ba(OR)_2*(ROH)_n$ which must be decomposed at high temperatures.

In Reaction (2) the metal is first dissolved in liquid ammonia (T<−33° C.) to form the amide and then successively to the alkoxide, which involves the disadvantages of a low temperature reaction.

Lastly, in Reaction (3) the production of the iodide is uneconomical.

The problem addressed by the invention is to overcome the disadvantages of the state of the art and prepare substances which permit the production of alkaline earth metal alkoxides by a relatively simple method.

The problem is solved by alkaline earth metal alkylene diamides, wherein Ba, Sr and Ca can be used as alkaline earth metals. Alkaline earth metal alkylene diamides can be easily reacted with an alcohol to form the corresponding alkaline earth metal alkoxide. Preferred alkaline earth metal alkylene diamides are derived from the primary alkylene diamines. Especially preferred are alkaline earth metal ethylene diamides.

Surprisingly it was found that the alkaline earth metals Ba, Sr and Ca can be dissolved very easily in ethylenediamine, whereupon the corresponding alkaline earth metal ethylenediamine and hydrogen are formed:

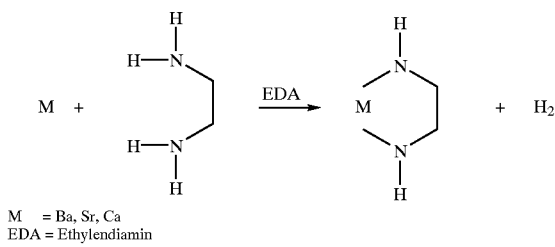

M = Ba, Sr, Ca
EDA = Ethylendiamin

DETAILED DESCRIPTION OF THE INVENTION

Preferably the alkaline earth metal in the form of powder, granules or pieces is fed into the ethylenediamine. The reaction is preferably performed under an inert gas atmosphere. Preferably the ethylenediamine is added to the alkaline earth metal in excess at a molar ratio of 2:1 to 50:1. A preferred reaction temperature is between 8.5° C. and 118° C., i.e., in the range in which ethylenediamine is fluid. In principle the reaction can also be performed at lower temperatures with solid ethylenediamine, as a solid state reaction, or at higher temperatures with gaseous ethylenediamine. Especially preferred is the temperature range of 10 to 40° C.; the reaction can also be performed advantageously at room temperature. A measure of the reaction rate is the evolving of hydrogen. The reaction rate of the exothermic reaction can be controlled by the rate of addition of the alkaline earth metal and to a limited extent by cooling the reaction vessel. The alkaline earth metal ethylene diamide precipitates as an insoluble, gray solid which can be isolated by filtration and/or concentration and drying.

The reaction can best be performed with barium as the alkaline earth metal and ethylenediamine as the alkylenediamine.

Basically, the reaction can also be performed with alkalinediamines other than ethylenediamine; of course the reaction rates in this case are slower; for example, several days are required at the boiling point at standard pressure to dissolve barium in propylenediamine (to form the barium propylenediamide). Acceleration of the reaction can be achieved by raising the temperature and simultaneously raising the pressure.

One application of the alkaline earth metal akylene diamides is their use in the synthesis of alkaline earth metal alkoxides.

For this purpose the alkaline earth metal alkylene diamides (here an alkaline earth metal ethylenediamide) is reacted with an alcohol to form the corresponding alkaline earth metal oxide.

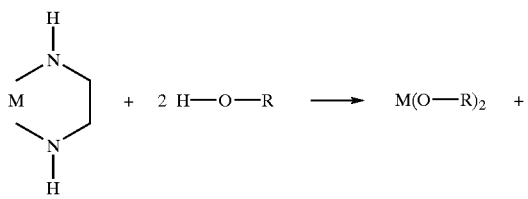

-continued

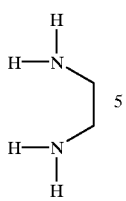

Preferred in that case is a stoichiometric amount of alcohol: nonstoichiometric amounts of alcohol lead to the desired product plus complex compounds. The reaction with alcohol can be performed undiluted, in residual excess alkylenediamine or in a solvent. The solvent can be aliphatic hydrocarbons (cyclic or acyclic) with 5 to 12 carbon atoms or aromatic hydrocarbons with 6 to 12 carbon atoms and/or ethers.

The hydrocarbons can be, for example, one or more of the compounds pentane, cyclopentane, hexane, heptane, octane, cyclohexane, toluene, xylene, cumene, ethylbenzene or Tetralin.

The ethers can be, for example, one or more of the compounds, tetrahydrofuran (THF), 2-methyl-THF, tetrahydropyran, diethylether, diisopropyl ether, dibutyl ether, dioxane, methyl-tert.butyl ether, glycol ethers (such as monoglymes, diglymes) or mixtures thereof.

An isolation of the alkaline earth alkoxide can be performed by concentration by evaporation and drying, in which case the alkylenediamine can be recycled. The alkaline earth alkoxide can be prepared either as a solid or it can be dissolved in a solvent and offered as a ready-to-use solution.

The invention is further explained below with the aid of examples.

DETAILED DESCRIPTION OF PREFERRED EMBODIMENTS

EXAMPLE 1

Preparation of Barium Ethylenediamide 700 g (1.65 mol) of ethylenediamine (EDA) is placed in a one-liter reaction flask with magnetic stirrer under argon at room temperature. Within 6 hours, 80 g (0.68 mol) of barium chips was added in portions. In the exothermic reaction the solution at first colored blue, and then turned to gray, and the barium ethylenediamide (Ba-EDA) precipitated. The hydrogen (0.58 mol) that formed was a measure of the reaction rate and indicated the end of the reaction. The reaction suspension obtained was concentrated at 100° C. in an oil pump vacuum. 120 g of Ba-EDA remained, with a content of 95%.

EXAMPLE 2

Preparation of Barium Ethylenediamide

As in Example 1, a Ba-EDA suspension was prepared and was filtered through a G-3 frit. The residue was dried at room temperature in an oil pump vacuum. The Ba-EDA obtained (126 g) had a content of 90%.

EXAMPLE 3

Preparation of Strontium Ethylenediamide

In a 500-ml reaction flask with magnetic stirrer, 16 g (0.18 mol) of strontium pieces were added to 220 g of EDA (3.66 mol) and stirred for several days until the hydrogen formation (0.18 mol) had ended. The gray reaction suspension obtained was concentrated at 120° C. in the oil pump vacuum. 28 g of Sr-EDA remained, as a 70% powder.

EXAMPLE 4

Preparation of Calcium Ethylenediamide 220 g EDA (3.66 mol) was treated with 7 g (0.18 mol) of calcium granules at room temperature under argon in a 500-ml reaction flask with magnetic stirrer, and stirred for 10 days at RT until the evolution of hydrogen ceased. Within this time 0.1 mol of the calcium had reacted to form a light gray powder (calcium ethylenediamide).

EXAMPLE 5

Preparation of Barium Propylenediamide 58 g of 1,3-propylenediamine (0.78 mol) was treated with 1.8 g (0.013 mol) of barium granules under argon at room temperature in a 250 ml reaction flask with magnetic stirrer.

The formation of hydrogen began slowly and the solution turned turbid due to barium propylenediamide precipitation. Over 4 days, 3.5 mmol of barium went into solution, which corresponds to a yield of 25%.

EXAMPLE 6

Preparation of Barium Tert-Butoxide 12 g of the Ba-EDA from Example 1 (95% pure, i.e., 58 mmol of Ba-EDA) was suspended in 175 g of cyclohexane and within 15 minutes a mixture of 8.7 g of tert-butanol (116 mmol) and 8.7 g of cyclohexane was added, and it was heated for 1 hour at ebullition to complete the reaction. After concentration at 120° C. in the oil pump vacuum, 17 g of barium tert.-butoxide remains as a light brown powder. This was divided into 3 portions, which were recrystallized from hexane, cyclohexane and toluene. The solubilities were as follows:

| | |
|---|---|
| Solubility in hexane | 5.9% |
| Solubility in cyclohexane | 11.3% |
| Solubility in toluene | 11.6% |

EXAMPLE 7

Preparation of Barium Tert-Amoxide 44 g of Ba-EDA from Example 1 (95% pure, i.e., 213 mmol Ba-EDA) was suspended in 1500 ml of cyclohexane and within 90 minutes, 38 g (430 mmol) of tert-amyl alcohol was added at room temperature, and then the mixture was refluxed for 1 hour. After concentration at 120° C. in an oil pump vacuum, 62 g of barium tert-amoxide remained as a light brown powder. This was divided into 3 portions, which were crystallized from hexane, cyclohexane and toluene.

| | |
|---|---|
| Solubility in hexane | 3.7% |
| Solubility in cyclohexane | 4.0% |
| Solubility in toluene | 3.4% |

EXAMPLE 8

Preparation of Barium 2-Ethylhexanolate

In a one-liter Schlenk flask 72 g of Ba-EDA from Example 1 (365 mmol) was suspended in 570 g of cyclohexane and within 3 hours 92.7 g of 2-ethylhexanol (712 mmol) was added. The reaction mixture warmed slightly from 25 to 30° C. and the barium 2-ethylhexanolate went into solution. The reaction mixture was concentrated at 120° C. and dried in the oil pump vacuum. The viscous oil remaining was dissolved in 400 g of cyclohexane and the excess Ba-EDA was filtered out. 510 g of solution was obtained with a content of 325 mmol of barium 2-ethylhexanolate, which corresponds to a yield of 91%.

The solubilities were found to be as follows:

| | |
|---|---|
| Solubility in hexane | 17.8% |
| Solubility in cyclohexane | 49.5% |
| Solubility in toluene | 16.6% |

What is claimed is:

1. An alkaline earth metal alkylene diamide, wherein said alkaline earth metal is selected from the group consisting of Ba, Sr, Ca.

2. An alkaline earth metal ethylenediamide, wherein said alkaline earth metal is selected from the group consisting of Ba, Sr, Ca.

3. Barium ethylenediamide.

4. A method for the preparation of an alkaline earth metal alkylene diamide, comprising the steps of dissolving an alkaline earth metal selected from the group consisting of Ba, Sr or Ca in an alkylenediamine, to form this corresponding alkaline earth metal alkylenediamide.

5. The method according to claim 4, wherein the alkylenediamine is added to the alkaline earth metal in an excess at a molar ratio of 2:1 to 50:1.

6. The method according to claim 4, wherein the reaction is conducted at a temperature up to 200° C. and a pressure up to 10 bar.

7. A method for the production of an alkaline earth metal oxide comprising forming an alkaline earth metal oxide from an alkaline earth metal alkylene diamide.

8. A method for producing alkaline earth metal alkoxides comprising the steps of dissolving in an alkylenediamine to form the corresponding alkaline earth metal alkylene diamide, and reacting said alkaline earth metal alkylene diamide with an alcohol to the alkaline earth metal alkoxide.

9. The method of claim 8, wherein the reaction is performed in a solvent.

10. The method of claim 9, wherein the solvent at least one solvent is selected from the group consisting of a hydrocarbon and an ether.

11. The method of claim 10, wherein said hydrocarbon is a cyclic or acyclic aliphatic hydrocarbon with 5 to 12 carton atoms or an aromatic hydrocarbon with 6 to 12 carbon atoms.

12. The method of claim 11, wherein the solvent is at least one hydrocarbon selected from the group consisting of pentane, cyclopentane, hexane, heptane, octane, cyclohexane, toluene, xylene, cumene, ethylbenzene and Tetralin.

13. The method of claim 10, wherein solvent is at least one ether selected from the group consisting of tetrahydrofuran (THF), 2-methyl-THF, tetrahydropyran, diethyl ether, diisopropyl ether, dibutyl ether, dioxane, methyl-tert-butylether and glycol ether.

* * * * *